United States Patent [19]

Fleck et al.

[11] Patent Number: 4,539,560
[45] Date of Patent: Sep. 3, 1985

[54] BED DEPARTURE DETECTION SYSTEM

[75] Inventors: David C. Fleck; Joseph H. Novak; Clement J. Koerber, Sr., all of Batesville, Ind.

[73] Assignee: Hill-Rom Company, Inc., Batesville, Ind.

[21] Appl. No.: 448,827

[22] Filed: Dec. 10, 1982

[51] Int. Cl.³ ............................................. G08B 21/00
[52] U.S. Cl. ................................... 340/573; 340/666
[58] Field of Search ............. 340/573, 666, 575, 667; 200/85 R; 73/172; 5/508

[56] References Cited

U.S. PATENT DOCUMENTS

| 3,766,344 | 10/1973 | Nevett | 340/667 |
| 3,991,414 | 11/1976 | Moran | 340/573 |
| 4,020,482 | 4/1977 | Feldl | 340/279 |
| 4,175,263 | 11/1979 | Triplett et al. | 340/573 |
| 4,195,287 | 3/1980 | McCoy et al. | 340/521 |
| 4,228,426 | 10/1980 | Roberts | 340/573 |
| 4,242,672 | 12/1980 | Gault | 340/573 |
| 4,295,133 | 10/1981 | Vance | 340/573 |

Primary Examiner—Jerry W. Myracle
Attorney, Agent, or Firm—Burns, Doane, Swecker & Mathis

[57] ABSTRACT

The disclosure relates to bed departure detection devices employing tape switch detectors in fixed positions in the seat and thigh sections of the mattress supporting structure of an articulated hospital bed. Bedside circuitry, connected to existing nurse call and two-way communication links, provides signals to a central nurse call station as an indication of unauthorized bed departure.

24 Claims, 7 Drawing Figures

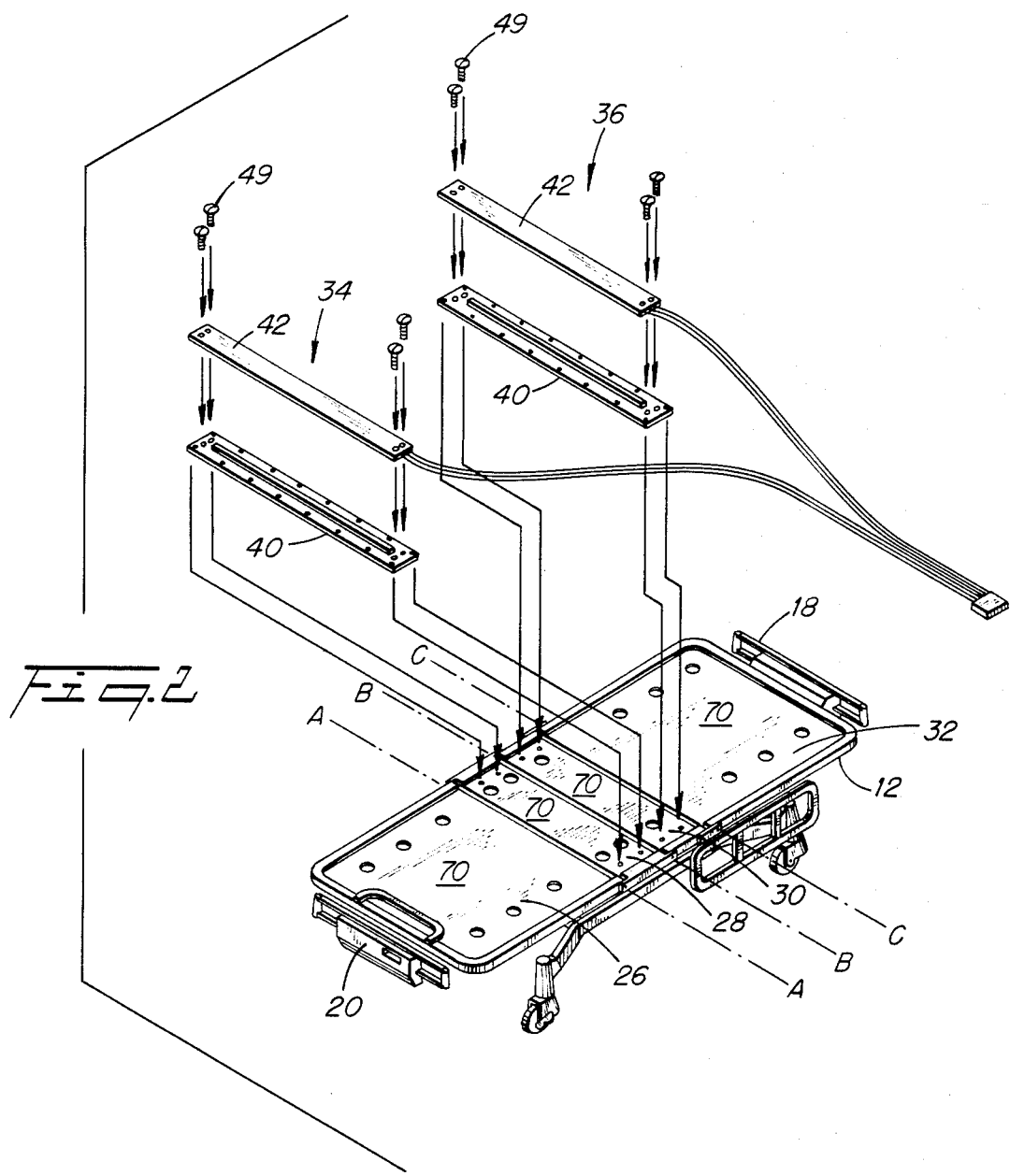

BED DEPARTURE DETECTION SYSTEM

BACKGROUND OF THE DISCLOSURE

The present invention relates to an apparatus useful in the detection of the presence or absence of a person in a bed. More particularly, the invention relates to detection devices incorporated in a hospital bed structure and external circuitry at bedside for relaying information to personnel at a central call board.

Unauthorized departures of patients from their beds are a serious problem in providing care to the sick and infirm. Prevention of these departures, and the falls which may result, require a high level of surveillance. If injury results, legal action may be taken against the health care personnel and the institution. The personnel or institution may be found liable, if reasonable precautions have not been taken to prevent the unauthorized departure or fall.

A number of different types of bed monitoring systems have been proposed. Most of such systems employ a movable detector which can be deployed in various positions under the bed mattress or under the bed covers. See, for example, the signal detector systems illustrated in U.S. Pat. No. 4,020,482 to Feldl and U.S. Pat. No. 4,295,133 to Vance. Other systems employ several pneumatic or electrical detectors incorporated into a movable mat or pad. Such systems are shown in U.S. Pat. No. 4,195,287 to McCoy et al; U.S. Pat. No. 4,175,263 to Triplett et al; U.S. Pat. No. 4,228,426 to Roberts; and U.S. Pat. No. 4,242,672 to Gault.

The aforementioned systems rely on manual positioning of the detector strip or mat in the bed. Aside from the effort required to effect installation, such systems suffer from several inherent defects. First, errors in positioning the detector may result in erroneous indications of the presence or absence of the patient in the bed. This is particularly true of signal detector systems which detect the patient's weight in a relatively small area in the bed. Improper handling of electrical tape switch detectors during repositioning may result in damage to the detector. In articulated beds, the adjustment of the bed may cause movement or bunching of the springs, mattress and/or detector which can result in erroneous indications.

It is an object of the present invention to provide a simply and inexpensively constructed bed departure detection apparatus which is permanently installed in the bed.

It is another object of the present invention to provide a multiple detector system in which detectors are installed in fixed, proper locations in the bed springs.

It is another object of the present invention to provide a multiple detector monitoring system for an articulated bed which minimizes erroneous indications caused by movement or bunching of the springs, mattress or detectors when the bed is adjusted.

Bed exit detector systems are shown in U.S. Pat. No. 3,325,799 to Farris and U.S. Pat. No. 3,991,414 to Moran which employ straps or wires stretched from point to point in arrays in the bed. The wires or straps are coupled to strain gauges or switch cartridges. Aside from its clear structural difference from the present invention, the Farris system is apparently not adapted for use in an articulated bed. The Moran system apparently requires that the detector system tension be adjusted when the articulated bed is set in a new position.

It is an object of the present invention to employ a permanently installed detector system for an articulated bed which does not require sensitivity adjustments when the bed is set in a new position.

Bed departure detection systems must quickly and accurately inform responsible health care personnel of patient movement so that falls or other hazards can be avoided. A number of the systems mentioned above employ external circuitry and existing nurse call signalling links to provide an indication of patient departure. Other external circuitry for this purpose is shown in Reissue Pat. No. 28,754 to Cook et al. It is useful for such systems to differentiate a bed exit signal from a patient initiated nurse call, so that higher priority bed departure indications will be recognized as such and distinguished from more routine calls.

It is an object of the present invention to provide an easily and inexpensively constructed interface between a bed detection apparatus and a remote, central call station, which clearly distinguishes a bed departure indication from other nurse calls.

It is another object of the present invention to provide a bedside external circuitry package which may be selectively used with a permanently installed bed departure detector and existing communication links to provide a quick and accurate indication of bed departure to responsible personnel at a remote location.

These and other objects and features of the present invention will become apparent from the claims and from the following description when read in conjunction with the accompanying drawings.

SUMMARY OF THE INVENTION

A bed apparatus is disclosed for supporting a mattress and including integral detectors incorporated in the supporting structure. More particular, the apparatus of the present invention includes a generally rectangular bed frame articulated at least two parallel axis extending across the width of the bed, i.e. from side to side. The bed articulations define at least a seat portion and a thigh portion of the bed. A first resilient tape switch and resilient backing plate is attached to the seat section of the bed and extends across substantially the entire width of the bed. Similarly, a second resilient tape switch and backing plate may be attached to the bed frame extending across substantially the entire width of the thigh section of the bed. Both tape switch assemblies partially support the mattress lying above and provide an indication of the weight carried by their respective overlying portions of the mattress. In this way two separate weight indications are obtained from fixed positions in the bed and signals from both switches may be electrically monitored to distinguish bed egress from momentary changes in weight distribution caused by the patient moving about on the bed. Because the switches are incorporated in the mattress supporting structure, virtually no unevenness need be induced in mattress surface. Because of the positioning of the tape switches on the articulated seat and thigh sections, the bed may be adjusted without altering the sensitivity of the switches.

The apparatus is effective in monitoring the presence or absence of a person in the bed. The use of two detectors, located in the thigh section and seat section, improves the accuracy of the system. It is highly likely that the patient has departed the bed, if no weight indication is produced by either the thigh or seat detector. In addition to monitoring bed departure, the apparatus may be used to monitor patient condition, for example, patient restlessness.

In a preferred embodiment of the present invention the tape switch assemblies are attached to the bed frame by means of a plurality of coil springs which suspend the backing plates and an interconnected wire mesh from the bed frame.

The tape switches may be electrically connected in parallel and connected to an external bedside circuit for producing a signal in response to the patient's presence or absence. The bedside circuit produces an alarm signal for transmission over a nurse call link to a central call board remote from the bed. In addition, the bed side package may include a circuit responsive to electrical indications from the detector tape switches for producing an audible bed departure indication over a two-way voice communication link between the bed and the central call board.

In a preferred embodiment of the present invention the bedside circuitry includes an RC time delay circuit which inhibits the production of an erroneous alarm signal in response to momentary reductions in weight on the switches caused by normal movement of the patient in the bed. The bedside circuit may also include latch and reset circuits which provide a continuing alarm signal until the circuit is manually reset at bedside.

BRIEF DESCRIPTION OF THE DRAWINGS

FIG. 2 is a partially exploded, pictorial view of a hard board, articulated hospital bed with two tape switch detectors, constructed according to the teachings of the present invention.

DETAILED DESCRIPTION

Figure 1:
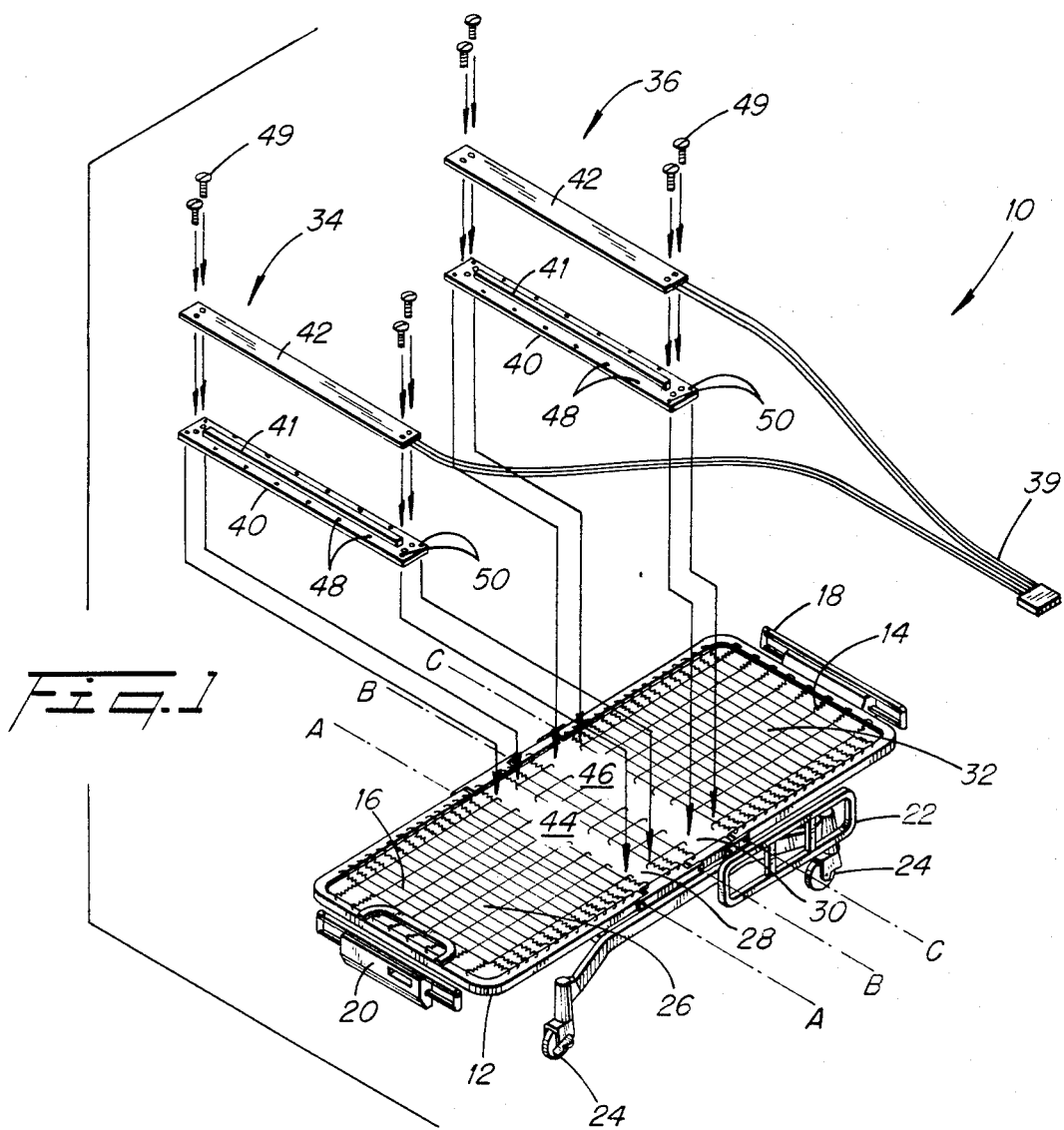
FIG. 1 is a partially exploded, pictorial view of an articulated hospital bed frame and spring apparatus with two tape switch detectors, constructed according to the teachings of the present invention.

Referring first to FIG. 1, an articulated bed frame and spring apparatus with two tape switch detectors is denoted generally by the numeral 10. In the embodiment shown in the figure, the apparatus includes a rectangular bed frame 12, an array of coil springs 14 about the periphery of the bed frame, and a wire mesh or fabric 16 suspended between the springs 14. A headboard mounting 18 is provided at the head of the bed and a footboard mounting 20 is provided at the foot of the bed. A guard rail 22 may be located on both sides of the bed frame. Wheels 24 are provided to facilitate movement of the bed.

The bed frame and spring apparatus of FIG. 1 is articulated to provide for adjustments for the comfort of the patient. More particularly, the bed frame is provided with three axes of articulation A, B and C. These axes of articulation define bed sections: axis A and the foot of the bed define a lower leg section 26; axes A and B define a thigh supporting section 28; axes B and C define a seat or buttock supporting section 30; and axis C and the head of the bed define a head section 32.

Figure 1A:
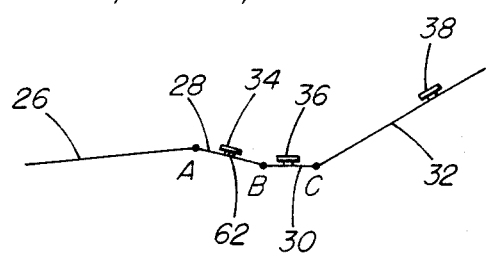
FIG. 1a is a schematic side elevation of an articulated bed with detector tape switches.

Tapes switch assemblies 34 and 36 may be attached to the bed frame 12 in the manner indicated in the figure. As shown more clearly in FIG. 1a, tape switch assembly 34 is located in the thigh section 28 approximately centrally between the axes A and B. Similarly tape switch assembly 36 is located in the seat section 30 approximately centrally between articulation axes B and C. Advantageously, at least one coil spring 14 should lie between an adjacent articulation axis and the coil spring or springs suspending the tape switch assembly. This arrangement inhibits erroneous indications caused by movement or bunching of the mesh or mattress when the bed is adjusted.

In an alternative embodiment of the present invention a third tape switch assembly 38 may be provided for location in the head section 32 of the apparatus.

With continued reference to FIG. 1 the tape switch assemblies 34 and 36 may comprise a flexible backing plate 40 and a tape switch 42, the construction of which will be described in greater detail in connection with FIGS. 1b, 1c and 1d. The backing plates 40 may be formed with a raised, longitudinal ridge 41 to provide increased sensitivity so that the switch assembly responds more readily to weight placed on the mattress. The tape switches 42 may be electrically connected in parallel to a flexible electrical lead 39 for connection to an external bedside circuit package (not shown in FIG. 1).

In the embodiment of FIG. 1, the flexible backing plates 40 are incorporated into the mesh and spring assembly of the bed. More particularly apertures 44 and 46 in the mesh 16 receive the switch assemblies. Holes 48 in the sides of the backing plates 40 are connected to adjoining mesh sections in the bed. Holes 50 in the ends of the backing plates 40 may be connected to edge portions of the mesh or directly connected to one or more of the coil springs 14. The tape switches 42 may be connected to their respective backing plates by means of threaded fasteners 49.

Figure 1B:
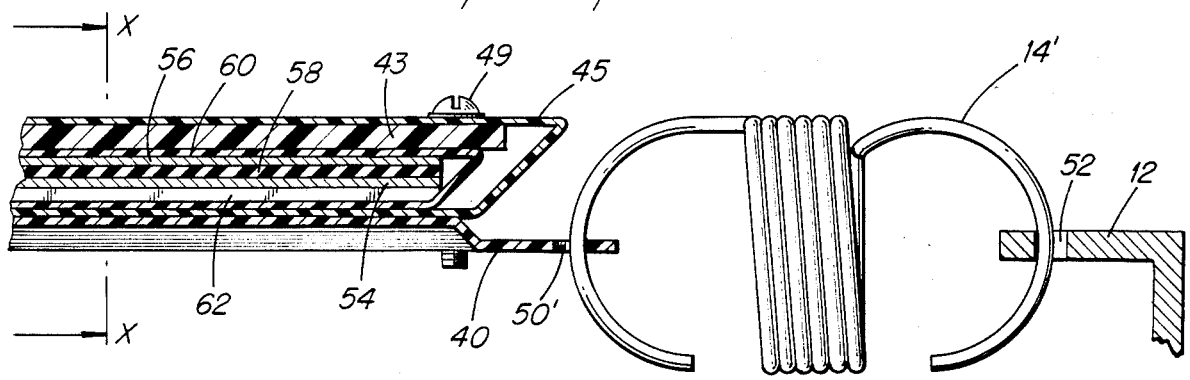
FIG. 1b is a cross-sectional side elevation detail of a spring and detector assembly structure which may be used in the apparatus of FIG. 1.

FIG. 1b is a side elevational detail showing a technique for connecting the tape switch assemblies 34 or 36 to the bed frame 12 by means of coil springs 14. The figure also illustrates the construction of the tape switch assembly. As shown in the figure, one end of coil spring 14' is inserted through an aperture 52 in the frame 12 and an opposite end of the coil spring 14' is inserted through an aperture 50' in the backing plate 40 of the tape switch assembly.

The tape switch 42 may include a pair of resilient metal conductors 54 and 56. The conductors are normally spaced from one another by means of insulators 58. The conductors are adapted to contact one another when at least a portion of the patient's weight is supported by the section of the bed in which the tape switch is located. The tape switch may also include a waterproof flexible housing 60 which encloses the conductors 54 and 56. A thickened ridge 62 may be formed in the housing 60 to facilitate contact between the mattress and the tape switch to improve sensitivity of the switch.

It will be readily understood that, when the patient lies on the bed, the mesh, backing plate, and tape switch will be compressed in locations beneath the patient. The compression of the tape switch results in contact at one or more places between the conductors 54 and 56 resulting in an electrical indication that the patient is in the bed. It has been found that accurate indications of the presence or absence of the patient may be obtained by sensing the patient's weight in at least two portions of the articulated bed: the seat section and thigh section. Accordingly, separate tape switch assemblies are located in both sections in a preferred embodiment of the present invention.

Figure 1C:
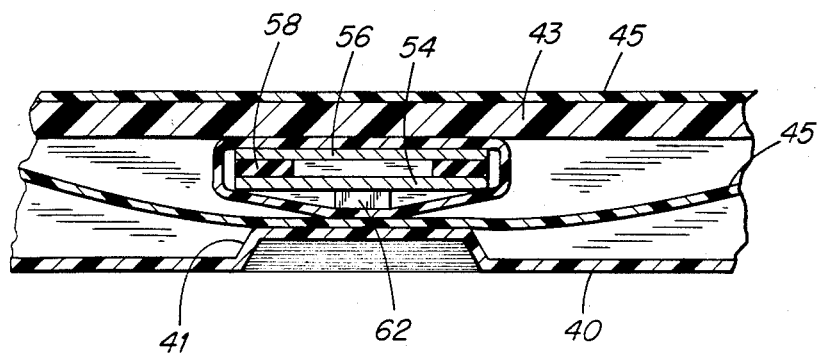
FIG. 1c is a cross-sectional view of the assembly of FIG. 1b taken along line x—x.

FIG. 1c is a cross-sectional detail of the assembly of FIG. 1b taken along line x—x, which illustrates the operation of the detector assembly. When weight is placed on the top of the switch, conductors 54 and 56 will be flexed by the ridge structure 62 and ridge 41. If the force is sufficient the conductors will touch, and the switch will be closed.

Figure 1D:
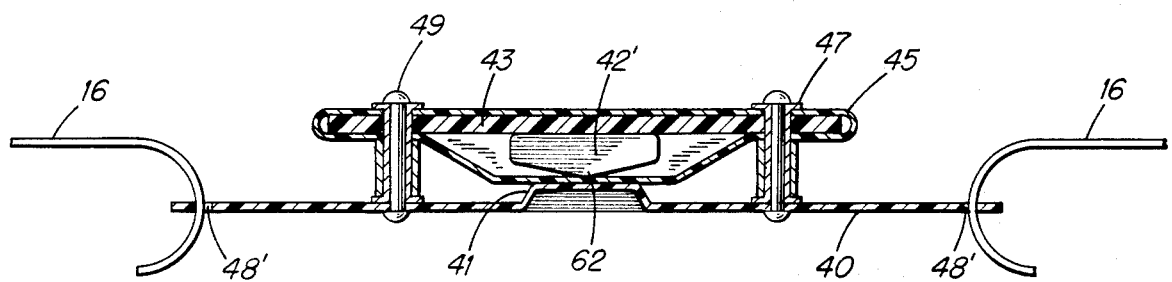
FIG. 1d is a cross-sectional view of the spring and detector assembly of FIG. 1b showing a means of attachment to the spring mesh or fabric.

FIG. 1d is a cross-sectional view of the detector assembly showing its attachment to the mesh or fabric 16. The tape switch 42', similar to that described in connection with FIG. 1b, is oriented with its thickened ridge 62 facing downward, away from the mattress. The tape switch is attached to a vinyl backing strip 43, and this combination is heat sealed in a waterproof vinyl cover or housing 45. Eyelets 47 pierce the housing and facilitate attachment to the metal backing plate 40, by means of the fasteners 49', extending therethrough. The wire mesh or fabric 16 is attached to the backing plate 40 through apertures 48'.

Referring now to FIG. 2, a hard board style hospital bed incorporating two fixed tape switch detectors is illustrated. In certain applications, it is desirable to use a firmer support for a hospital bed mattress i.e., a support firmer than the standard spring and mesh structure such as disclosed in connection with FIG. 1. It is, nevertheless, possible to adapt the tape switch assemblies discussed in connection with FIG. 1 for use on such a hardboard bed. In FIG. 2 the attachment of the tape switches to such a bed is illustrated. In FIG. 2 structures similar to those shown in FIG. 1 are identified by like numerals. In the hardboard bed frame, rigid planar boards 70 are substituted for the springs and mesh employed in the bed of FIG. 1. It will be seen from the figure that a first tape switch assembly 34 is attached to the thigh section 28 of the hardboard bedframe and a second tape switch assembly 36 is attached to the seat section 30 of the hardboard bedframe. The tape switch assemblies 34 and 36 may be attached to the hardboards by means of screw fasteners 49 as shown in the figure. In this embodiment, discrete backing plates 40 may be omitted. If the backing plate is omitted, a ridge or bead may be placed or formed on the hardboard to facilitate operation of the tape switch in the manner discussed in connection with FIG. 1c.

Figure 3:
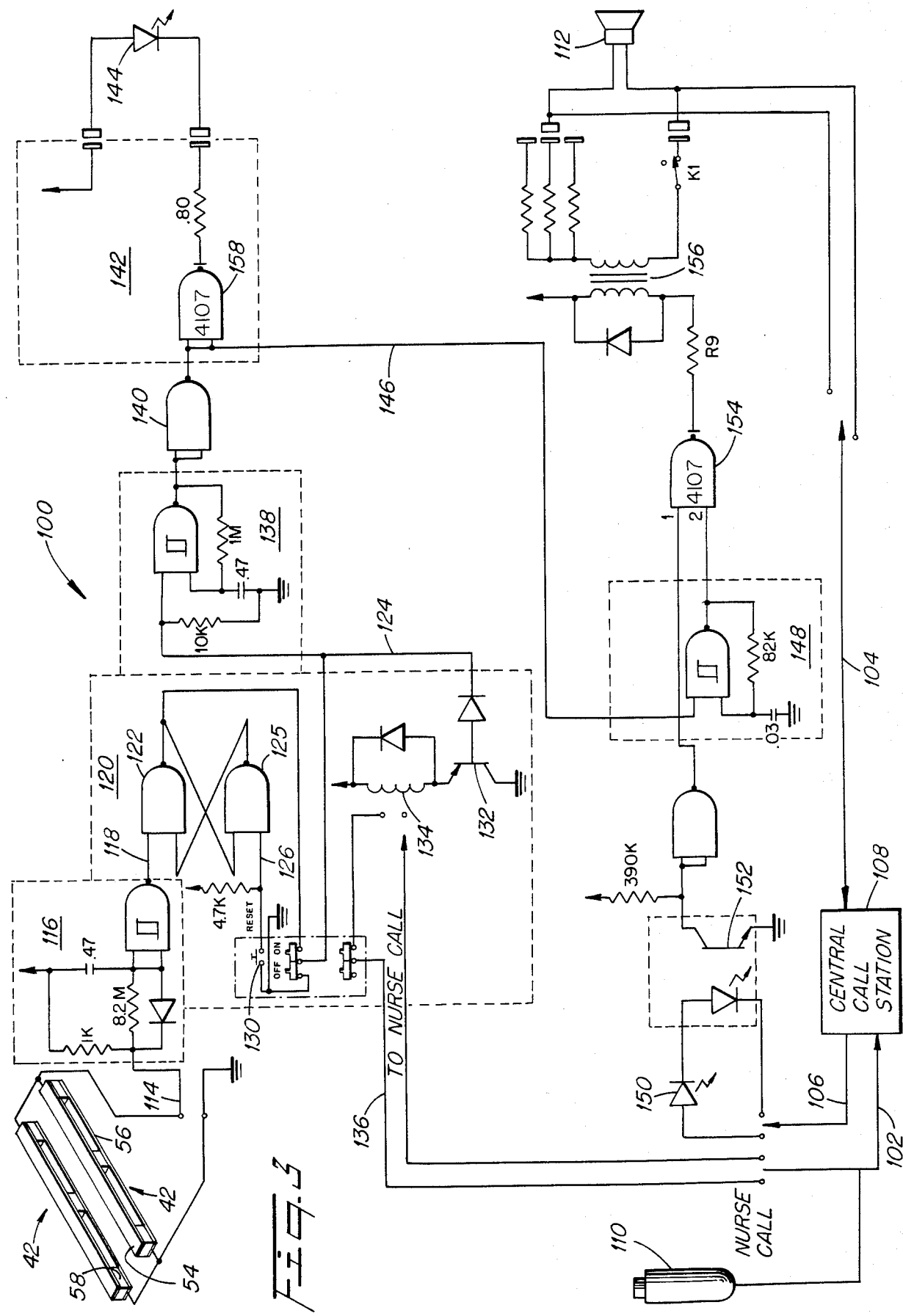
FIG. 3 is a schematic circuit diagram of a bedside circuitry package interconnecting bed mounted tape switches with nurse call and two-way communication links to a central call station.

FIG. 3 is a schematic circuit diagram of a bedside circuitry package 100 interconnecting the bed tape switches 42 with a nurse call communication link 102, with a two way voice communication link 104, and with a privacy light communication link 106. The communication links are shown terminating at a central call station 108. Communication links from other beds would, likewise terminate at the central call station.

In many health care facilities dedicated communication lines are installed between bed areas and remote nurse call stations where the condition of a number of patients can be monitored simultaneously by the same personnel. In many instances these communications links include two conductor nurse call links which permit the patient to call a nurse by pressing a button such as that identified by the numeral 110. These same installations may include two-way voice communication links to the central call station including a microphone-speaker system 112 located in proximity to the patient's bed.

In a preferred embodiment of the present invention a plurality of detector tape switches, permanently installed in the patient's bed, are interconnected by means of the bed side external circuitry package 100 to use the existing communication links already running to the patient's bedside in a manner which permits the central call station 108 to be signaled in the event that an unauthorized departure from the bed occurs.

As shown in FIG. 3, two tape switches 42 may be connected in parallel in such a way that the input terminal 114 of the bedside package 100 is grounded if either of the tape switches 42 are closed by the weight of the patient. This electrical connection in parallel prevents the erroneous indications which would otherwise result if the patient's weight shifted substantially away from a single detector located only in the thigh section or only the seat section of the articulated bed. It is only if a closure does not occur in either tape switch that a signal is produced indicative of a patient departure.

The input terminal 114 of the bedside package 100 is connected to an RC time delay circuit 116. An indication of unauthorized departure appears at the output terminal 118 of the RC time delay circuit 116 only if both switches are open for a preset, time interval. This time delay is incorporated into the system to prevent erroneous indications of departure occuring as a result of momentary shifts in weight on the bed. Typically the time constant of the delay circuit is less than 10 seconds.

The output terminal 118 of the RC time delay circuit 116 is connected to a latch and reset circuit 120. The latch portion of the circuit includes NAND gates 122 and 125 which are coupled together to produce an indication of departure from the bed in response to an output signal of the RC time delay circuit. When the latch circuit is activated by the opening of both switches 42, it produces a signal indicative of a departure having occurred which is imposed on bus 124. The signal remains until the bedside package is manually reset by grounding the input terminal 126 of NAND gate 125 by actuation of reset switch 130 at bedside. This arrangement requires that a nurse or other personnel visit the bedside in order to cancel the alarm produced by the system.

The bus 124 is connected to a relay driver transistor 132 which, when deenergized by patient exit signal, deenergizes relay 134 and places a call on the nurse call line 136. The call is transmitted to the central call station by a two leaded nurse call communication link 102 as discussed above. Simultaneously, the signal on bus 124 energizes a subaudio frequency generating circuit 138. An output signal from the circuit 138 is inverted by means of inverter 140 and applied to a light driver circuit 142. The light driver circuit 142 illuminates a light emitting diode 144 located in the vicinity of the bed as a visible indication of an unauthorized departure having occurred. In addition, the inverter 140 energizes bus 146 which intermittently actuates an audio oscillator circuit 148.

When the nurse call signal is received via communication link 102 at the central call station, an indication is presented to personnel of a call having been placed from the bed area. This indication may take the usual form of an illuminated light or audible warning. The personnel now may choose to visit the bedside or to interrogate the system to determine whether the nurse call was patient actuated or actuated by the bed departure detection circuit. If a latter course of action is chosen, the hospital personnel may interrogate the system by means of the two way voice communication link 104.

Normally, the two way communication link is used by personnel at the central call station for communicating verbally with persons at the bedside. In order to insure privacy, many systems include a communication link 106 which illuminates a red privacy light 150 which informs people at bedside that conversations may be overheard at the central station.

In an embodiment of the present invention, the privacy light link and two way communication link are used to provide an audible indication at the central call station that an unauthorized departure has occurred. The interrogation begins by activation of the two way communication link. This actuates an opto-coupler 152 connected in series with a privacy light 150. A signal from the opto-coupler is applied to NAND gate 154. If both the privacy light is illuminated and an audio frequency is being generated by the audio frequency oscillator circuit 148, a pulsing audio frequency signal is applied to the audio transformer 156. This imposes an audio frequency signal on the microphone 112 of the two way communication system, with the result that an intermittent audio frequency alarm signal is carried by way of the two way communication link 104 back to the central call station to inform personnel at the central call station that an unauthorized departure has occurred.

Advantageously, similar NAND gates combined in an integrated circuit package can be used in the circuit in FIG. 3. In a preferred embodiment, all of the NAND gates with the exception of NAND gates 154 and 158 may be Schmitt NAND gates provided in groups of four in an integrated circuit designated by the device number 4093. NAND gates 154 and 158 may be NAND gates with higher current driving capacity such as the NAND gate manufactured by RCA under the device No. 40107.

By means of the foregoing, articulated hospital beds may be permanently equipped with plural, fixed position tape switch detectors for providing indication of unauthorized bed departure. In instances where bed departures are to be monitored, the bedside external circuitry package 100 may be connected to the detector-equipped beds and simultaneously connected to existing communication links with the central call station to provide the needed monitoring.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. Detection apparatus for an articulated bed having at least two articulated sections for supporting a mattress, each section including a rigid frame, comprising:

a first tape switch attached to a thigh supporting section of the bed and suspended from the frame across the width of the bed underneath of and in contact with the mattress;
a second tape switch attached to a seat supporting section of the bed and suspended from the frame across the width of the bed underneath of and in contact with the mattress;
said tape switches being separately actuable by the weight of a person on the respective sections of the bed to which the switches are attached; and
said tape switches being electrically connected and adapted to cooperate with an external electrical circuit for producing a signal in response to the person's weight shifting off of the sections to which the switches are attached.

2. The apparatus of claim 1 wherein the first and second tape switches are closed by the weight of the patient on the respective bed sections to which the switches are attached and wherein the tape switches are electrically connected in parallel so that a bed departure indication is produced when the switches are simultaneously opened.

3. The exit detection apparatus of claim 1, further comprising a third tape switch located in a head supporting portion of the bed.

4. Detection apparatus for an articulated bed having at least two articulated sections including a wire mesh attached to a bed frame by a plurality of springs, said articulated sections supporting a mattress and including a thigh supporting section of the bed and a seat supporting section of the bed, comprising:

a first tape switch located in said thigh supporting section of the bed and mounted on a first supporting plate suspended from the frame by springs;
a second tape switch located in said seat supporting section of the bed and mounted on a second supporting plate suspended from the frame by springs;
said first and second tape switches extending substantially across the width of the bed and being separately actuable by the weight of a person on the respective section of the bed in which the switches are located; and
said tape switches being electrically connected and adapted to cooperate with an external electrical circuit for producing a signal in response to the person's weight shifting off of the sections in which the switches are located.

5. The exit detection apparatus of claim 4 wherein each tape switch comprises a first resilient metal conductor separated from an approximately parallel, second resilient metal conductor by insulators spaced along the length of the tape switch, said conductors and insulators being enclosed in a waterproof, flexible housing; and wherein said supporting plates are made of resilient metal adapted to bend under the weight of the patient to thereby permit the first and second resilient metal conductors to contact each other at one or more locations between the spaced insulators.

6. A departure detection system for a hospital patient bed having at least two articulated frame and spring sections for supporting a mattress comprising:

a first switch, attached to the frame of one section of the bed and suspended from the frame across the width of the bed underneath of and in contact with the mattress, said first switch comprising a pair of resilient conductors normally spaced from one another and adapted to contact one another when at least a portion of the patient's weight is supported by said one section of the bed;

a second switch, attached to the frame of another section of the bed and suspended from the frame across the width of the bed underneath of and in contact with the mattress, said second switch comprising a pair of resilient conductors normally spaced from one another and adapted to contact one another when at least a portion of the patient's weight is supported by said another section of the bed, said first and second switches being electrically connected in parallel to circuitry for producing an electrical indication that the patient has departed the bed;

means responsive to said electrical indication of producing an alarm signal for transmission over a nurse call link to a central call board remote from said bed; and means responsive to said electrical indication from said switches for producing an audible bed departure indication over a two-way voice communication link between the bed and the central call board.

7. The detection system of claim 6 wherein the means for producing the alarm signal comprises:
   an RC time delay circuit having an input terminal, to which said switches are connected; and
   a latch and reset circuit for producing the alarm signal until reset.

8. The detection system of claim 7 wherein the time delay of the RC time delay circuit is selected to prevent erroneous indications of bed exit caused by movements of the patient in the bed which momentarily reduce the weight on both switches.

9. The detection system of claim 7 wherein the latch and reset circuit includes a relay for transmitting the alarm signal to the central call board over the nurse call communication link.

10. The detection system of claim 7 wherein said audible indication producing means includes an audio frequency oscillator and means for coupling the audio oscillator to a microphone of the two-way voice communication link.

11. The detection system of claim 10 further comprising a sub-audio frequency generator for flashing a bedside indicator light and connected to said audio frequency oscillator for producing repeating tone bursts coupled into the two-way voice communication link.

12. The detection system of claim 7 wherein said audible indication is produced in response to said alarm signal and an indication that the two-way voice communication link with the central call board is being used.

13. The detection system of claim 12 wherein the indication that the two-way voice communication link is being used is a privacy light.

14. A bed frame and spring apparatus with integral detectors for detecting the presence or absence of a person in the bed, comprising:
   an articulated bed frame having a thigh frame section and a seat frame section selectively moveable with respect to said thigh frame section;
   springs attached to the bed frame;
   mesh suspended from said springs for supporting a mattress, including a thigh mesh section attached to the thigh frame section and a seat mesh section attached to the seat frame section;
   a first tape switch means for providing an indication of the weight carried by the thigh section of the bed, said first tape switch means being suspended from the thigh frame section by at least one of said springs on each side of the bed;
   a second tape switch means for providing an indication of the weight carried by the seat section of the bed, said second tape switch means being suspended from the seat frame section by at least one of said springs and each side of the bed; and
   an electrical lead means for connecting the first and second tape switch means in parallel and for connecting the switches to an external sensing circuit.

15. The apparatus of claim 14 wherein the articulated bed frame includes a head section moveable with respect to said thigh section, and a lower leg section moveable with respect to said thigh section, and wherein a third tape switch means for providing an indication of the weight carried by the bed section of the bed, is suspended from the head frame section by at least one of said springs on each side of the bed.

16. The assembly of claim 14 wherein the tape switch means comprise:
   a backing plate extending across substantially the entire width of the bed and located approximately centrally between axes of articulation defining the bed section;
   a first resilient metal conductor extending across substantially the entire width of the bed;
   a second resilient metal conductor extending across substantially the entire width of the bed, approximately parallel to and spaced from the first resilient metal conductor;
   a plurality of insulators between the first and second conductors and spaced at intervals along the conductors; and
   a waterproof, flexible, nonconductive housing, enclosing said conductors and insulators, and attached to said backing plate.

17. A bed apparatus for supporting a mattress and including integral detectors comprising:
   a generally rectangular bed frame, articulated at three parallel axes extending across the width of the bed to define head, seat, thigh and lower leg sections of the bed;
   first resilient tape switch means, attached to the bed frame and extending across substantially the entire width of the seat section of the bed, for at least partially supporting the mattress and providing an indication of the weight carried by the seat section of the bed; and
   second resilient tape switch means attached to the bed frame and extending across substantially the entire width of the thigh section of the bed, for partially supporting the mattress and providing an indication of the weight carried by the thigh section of the bed.

18. The apparatus of claim 17 wherein the tape switch means are attached to the bed frame by a plurality of coil springs.

19. The apparatus of claim 17 further comprising a mesh suspended from the frame by a plurality of springs extending around the periphery thereof.

20. The apparatus of claim 19 wherein the tape switch means are attached to the bed frame by a portion of the mesh and the coil springs.

21. The apparatus of claim 19 wherein the first tape switch means is located approximately centrally in the seat section of the bed between the axes of articulation defining the seat section of the bed, at least one spring separating the springs suspending the tape switch means from each axes of articulation; and wherein the second tape switch means is located approximately centrally in the thigh section of the bed between the axes of articulation defining the thigh section of the bed, at least one spring separating the springs suspending the tape switch means from each axis of articulation.

22. Detection apparatus for a bed having a wire mesh attached to a frame by a plurality of springs for supporting a mattress, comprising a tape switch attached to the bed and mounted on a supporting plate suspended by springs from the frame across the width of the bed underneath of and in contact with the mattress, said tape switch being actuable by the weight of a person on the bed, said tape switch being electrically connected and adapted to cooperate with an external electrical circuit for producing a signal in response to the person's weight shifting off of the bed.

23. The apparatus of claim 22, wherein said bed includes at least two articulated sections, each section including a rigid frame.

24. Detection apparatus for an articulated bed having at least two articulated sections for supporting a mattress, each section including a rigid planar board, comprising:
- a first tape switch mounted on the rigid planar board of a first articulated section between said board and said mattress, and extending substantially across the width of the bed;
- a second tape switch mounted on the rigid planar board of a second articulated section between said board and said mattress, and extending substantially across the width of the bed;
- said first and second tape switches being separately actuable by the weight of a person on the respective articulated sections on which the switches are mounted; and
- said tape switches being electrically connected and adapted to cooperate with an external electrical circuit for producing a signal in response to the person's weight shifting off of the sections on which the switches are mounted.

* * * * *